United States Patent [19]

Morel

[11] Patent Number: 4,906,414
[45] Date of Patent: Mar. 6, 1990

[54] CHLORINATED β-KETOESTERS

[75] Inventor: Didier Morel, Lyons, France

[73] Assignee: Rhone-Poulenc Sante, Courbevoie, France

[21] Appl. No.: 303,082

[22] Filed: Jan. 25, 1989

Related U.S. Application Data

[63] Continuation of Ser. No. 450,267, Dec. 16, 1982, abandoned.

[30] Foreign Application Priority Data

Dec. 18, 1981 [FR] France ................ 81 23684

[51] Int. Cl.⁴ .......................................... C07C 69/738
[52] U.S. Cl. .................................. 260/408; 560/174; 568/394
[58] Field of Search ................. 560/174; 562/577; 260/408

[56] References Cited

U.S. PATENT DOCUMENTS 3,277,147 10/1966 Machleidt et al. ................ 360/128

OTHER PUBLICATIONS

Karrer, P. et al, Chem. Abstracts, 46:2550e, 1952.
Kosower et al, J. Organic Chemistry, 28, 630–33, 1963.
Tetrahedron Letters No. 40 (Oct. 1972), P. L. Slotter, pp. 4067–4070.

Primary Examiner—Vivian Garner
Attorney, Agent, or Firm—Stevens, Davis, Miller & Mosher

[57] ABSTRACT

New chlorinated β-ketoesters of the formula:

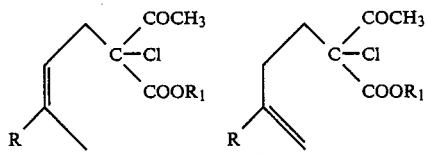

wherein R represents alkyl of 1 through 6 carbon atoms or alkenyl of 2 through 6 carbon atoms, and $R_1$ represents alkyl of 1 through 4 carbon atoms, their preparation and their use for the preparation of ethylenic ketones of the formula:

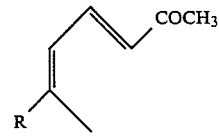

wherein R is as hereinbefore defined.

1 Claim, No Drawings

CHLORINATED β-KETOESTERS

This application is a continuation of application Ser. No. 450,267, filed Dec. 16, 1982 now abandoned.

The present invention relates to new chlorinated β-ketoesters of the general formula:

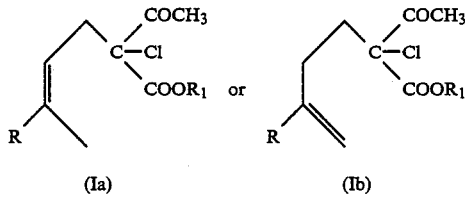

wherein R represents an alkyl radical containing 1 to 6 carbon atoms or an alkenyl radical containing 2 to 6 carbon atoms, and $R_1$ represents an alkyl radical containing 1 to 4 carbon atoms, and to their preparation and their use.

The ketoesters of general formula (Ia) or (Ib) are of real industrial and economic value insofar as they are used as intermediates for the synthesis of vitamins or perfumes. More particularly, the ketoesters of general formula (Ia) or (Ib) wherein R represents the 4-methylpent-3 enyl radical is an intermediate for the synthesis of pseudo-ionone, which is useful for preparing vitamin A.

It is known, in particular from E. W. WARNHOFF et al., Organic Syntheses, Coll. Vol. IV, 162 (1963), to prepare α-chloroketones by reaction of sulphuryl chloride with the corresponding ketone, but, when the ketone is unsaturated, addition of chlorine on to the double bond takes place. According to E. M. KOSOWER et al., J. Org. Chem., 28, 630 and 633 (1963), the halogenation of saturated or unsaturated ketones can be carried out by means of a cupric halide, preferably cupric chloride, in the presence of lithium chloride, the reaction being carried out in dimethylformamide at a temperature between 80° and 90° C. However, the use of a process of this type generally leads to polyhalogenated products and the yields are not quantitative.

According to the present invention, the chlorinated β-ketoesters of general formula (Ia) or (Ib) are obtained by reaction of cupric chloride with a compound of the general formula:

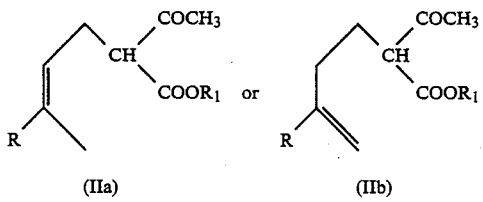

(wherein R and $R_1$ are as hereinbefore defined) in the presence of lithium chloride, the reaction being carried out at a temperature between 15° and 50° C. in a basic polar aprotic solvent such as N-methylpyrrolidone, dimethylformamide, dimethylacetamide, tetramethylurea or hexamethylphosphotriamide. It is particularly advantageous to carry out the reaction in N-methylpyrrolidone.

In general, the halogenation is carried out by means of an excess of cupric chloride in the presence of a virtually stoichiometric amount of lithium chloride. In this way, the products of general formula (Ia) or (Ib) are obtained with virtually quantitative yields and without the formation of polyhalogenated products.

The compounds of general formula (IIa) or (IIb) can be obtained by selective addition of a ketoester of the general formula:

(wherein $R_1$ is as hereinbefore defined) on to a butadiene of the general formula:

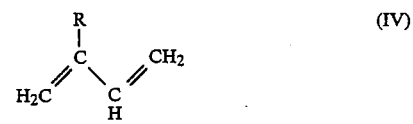

wherein R is as hereinbefore defined.

In general, the reaction is carried out in water, or in an aqueous-alcoholic medium containing at most 50% of an aliphatic alcohol containing 1 to 3 carbon atoms, in the presence of a catalyst consisting on the one hand of at least one water-soluble phosphine, and on the other hand of at least one transition metal compound, the catalyst being in solution in water and the transition metal compound being a rhodium compound.

Suitable water-soluble phosphines are those described in French Patent 76 22824 and more particularly those which correspond to the general formula:

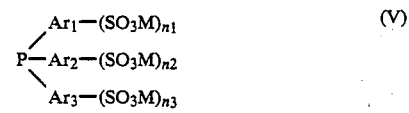

wherein $Ar_1$, $Ar_2$ and $Ar_3$, which are identical or different, each represent a radical selected from amongst the group comprising optionally substituted phenylene radicals and naphthylene radical, M represents a cationic radical of inorganic or organic origin, so selected that the phosphine of general formula (V) is water-soluble, and $n_1$, $n_2$ and $n_3$, which are identical or different, represent zero or an integer 1, 2 or 3, at least one of $n_1$, $n_2$ and $n_3$ being greater than or equal to 1.

The rhodium compound used must be water-soluble or capable of dissolving in water under the reaction conditions by means of a coordination reaction with the water-soluble phosphines. $RhCl_3$ and [RhCl(-cycloocta-1,5-diene)]$_2$ are of very particular value.

The amount of rhodium compound used is such that the number of gram atoms of elementary rhodium per liter of reaction solution is between $10^{-4}$ and 1.

The amount of phosphine is selected so that the number of gram atoms of trivalent phosphine relative to one gram atom of rhodium is between 0.1 and 200.

The minimum amount of water is that which is sufficient to dissolve all the catalyst and at least part of the reactants.

The reaction temperature is generally below 200° C. and is preferably between 50° C. and 125° C.

It is particularly advantageous to carry out the reaction in the presence of an excess of the ketoester of general formula (III), relative to the butadiene of general formula (IV).

To improve the reactivity, it is possible to add an inorganic base (alkali metal or alkaline earth metal hydroxides, carbonates or bicarbonates) or an organic base (aliphatic or aromatic tertiary amines) to the reaction medium at a concentration of between 0.005 and 5 mols of base per liter of aqueous solution.

The chlorinated β-ketoester products of general formula (Ia) or (Ib) are particularly useful for preparing the ethylenic ketones of the general formula:

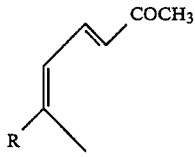

(wherein R is as hereinbefore defined) in the form of a mixture of the E,E or E,Z isomers.

The process for the preparation of the ethylenic ketones of general formula (VI) consists in decarboxylating a chlorinated β-ketoester of general formula (Ia) or (Ib) to give an a-chloroketone of the general formula:

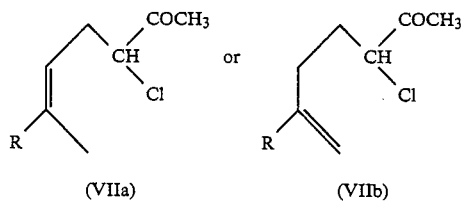

(wherein R is as hereinbefore defined) which is dehydrohalogenated to give an ethylenic ketone product of general formula (VI).

According to the present invention, the decarboxylation and dehydrohalogenation reactions can be carried out without isolating the α-chloroketone of general formula (VIIa) or (VIIb).

It is known, in particular from A. P. KRAPCHO et al., J. Org. Chem. 43 (1), 138 (1978), to decarboxylate gem-diesters, β-ketoesters or α-cyanoesters in the presence of an excess of an inorganic salt such as lithium chloride, the reaction being carried out in aqueous dimethyl sulphoxide at the reflux temperature of the reaction mixture.

Furthermore, it is known, in particular from E. W. WARNHOFF et al., Organic Syntheses, Coll. Vol. IV, 162 (1963), to dehydrohalogenate an α-halogenoketone in the presence of lithium chloride, in dimethylformamide at a temperature of about 100° C.

It has now been found that the α-chloro-β-ketoesters of general formula (Ia) or (Ib) lead to the α-chloroketones of general formula (VIIa) or (VIIb), with virtually quantitative yields, by treatment with lithium chloride, in a basic polar aprotic solvent such as N-methylpyrrolidone, dimethylformamide, dimethylacetamide, tetramethylurea or hexamethylphosphotriamide (preferably N-methylpyrrolidone), at a temperature of about 130° C., in the presence of water or a strong inorganic acid such as hydrochloric acid or sulphuric acid. It is particularly advantageous to carry out the reaction in the presence of a strong inorganic acid in order to avoid the secondary deacylation reaction.

In general, the reaction is carried out in the presence of a molar amount of lithium chloride, representing about 1 to 5 times the molar amount of the ketoester of general formula (Ia) or (Ib). Preferably, the amount of lithium chloride used is approximately the stoichiometric amount.

The amount of water or inorganic acid is approximately the stoichiometric amount.

Depending on the composition of the reaction mixture, the decarboxylation is complete after a heating time between 10 minutes and 5 hours at a temperature of about 100° C.

The α-chloroketones of general formula (VIIa) or (VIIb) are preferably converted to the ethylenic ketones of general formula (VI) by heating in the presence of lithium chloride, in a basic polar aprotic solvent such as N-methylpyrrolidone, dimethylformamide, dimethylacetamide or hexanethylphosphotriamide (preferably N-methylpyrrolidone), optionally in the presence of a very basic tertiary amine such as 2,4,6-trimethylpyridine (collidine) or ethyldicyclohexylamine. The molar amount of the tertiary amine represents about 1 to 5 times the molar amount of the ketoester of general formula (Ia) or (Ib). Preferably, the amount of tertiary amine used is approximately twice the stoichiometric amount. The dehydrohalogenation reaction is generally complete after a heating time of 1 to 20 hours at a temperature between 80° and 160° C.

To carry out the process according to the invention more conveniently, it is particularly advantageous to carry out the decarboxylation and dehydrohalogenation reactions without intermediate isolation of the α-chloroketone of general formula (VIIa) or (VIIb), using the system lithium chloride/inorganic acid/tertiary amine in solution in N-methylpyrrolidone, at a temperature between 80° and 160° C. for 1 to 20 hours.

The ketones of general formula (VI) which are obtained by the process of the present invention can optionally be purified by -physico-chemical methods such as distillation or chromatography.

The following non-limitative Examples illustrate the present invention.

EXAMPLE 1

Chlorination of a mixture of (IIa$_1$) and (IIb$_1$)

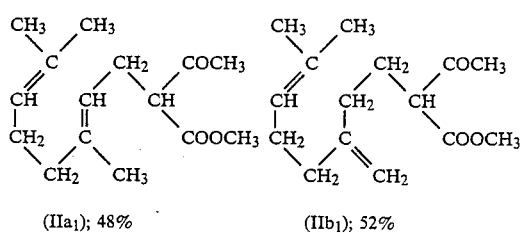

A mixture of (IIa$_1$) and (IIb$_1$) (24.66 g; 0.102 mol) is added to a mixture of cupric chloride (32.3 g; 0.24 mol) and lithium chloride (5.1 g; 0.12 mol) in N-methylpyrrolidone (100 cc). The reaction mixture is kept at 20° C. for 91 hours. The reaction mixture is then diluted by adding water (600 cc). The cupric chloride which has precipitated is filtered off and the reaction mixture is then extracted with pentane (2 x 50 cc). After the organic layers have been dried over sodium sulphate and concentrated under reduced pressure, a mixture of (Ia$_1$) and (Ib$_1$) (28.39 g) is obtained, the purity of which is of the order of 95% and which has the following characteristics:

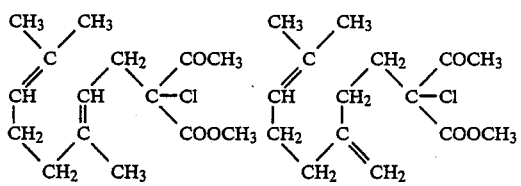

(Ia₁); 45%   (Ib₁); 55% b.p. $_{0.027}$ kPa (mixture) = 120° C.
chlorine content of the mixture = 12.4%.

The degree of conversion of the mixture of (IIa₁) and (IIb₁) is equal to 95%; the selectivity is equal to 100%.

The mixture of the products of the formulae (IIa₁) and (IIb₁) can be prepared in the following manner.

[RhCl(cycloocta-1,5-diene)]₂ (40.8 mg; 0.165 milligram atom of rhodium),

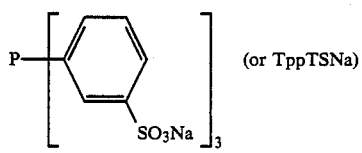

(or TppTSNa)

(2.2 g; 3.256 milligram atoms of $P^{3+}$), sodium carbonate (78.2 mg; 0.68 millimol), water (15 cc) and methanol (5 cc) are introduced into a stainless steel reactor purged with argon beforehand. Myrcene (15.92 g; 0.117 mol) and methyl acetate (13.9 g; 0.120 mol) are then introduced.

The mixture is heated at 90° C. for 1 hour, with stirring.

After treatment of the reaction mixture, a mixture of the products of the formulae (IIa₁) and (IIb₁) (12.488 g) is obtained.

EXAMPLE 2

Chlorination of a mixture of (IIa₂) and (IIb₂)

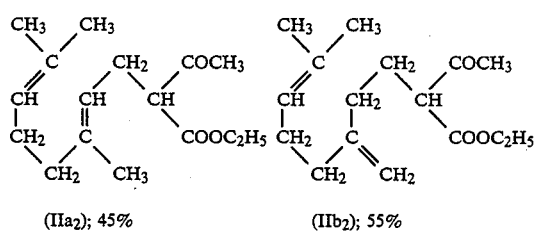

(IIa₂); 45%   (IIb₂); 55%

A mixture of the compounds of formulae (IIa₂) and (IIb₂) (107 g; 0.102 mol) is added to a mixture of cupric chloride (120 g; 0.89 mol) and lithium chloride (17 g; 0.4 mol) in N-methylpyrrolidone (300 cc). The reaction mixture is kept at 20° C. for 90 hours. The reaction mixture is then diluted by adding cold water (2 liters). The cuprous chloride which has precipitated is filtered off and the reaction mixture is then extracted with pentane (2 x 200 cc). After the organic layers have been dried over sodium sulphate and concentrated under reduced pressure, a mixture of the products of the formulae (Ia₂) and (Ib₂) (119 g) is obtained, the purity of which is of the order of 92% and which has the following characteristics:

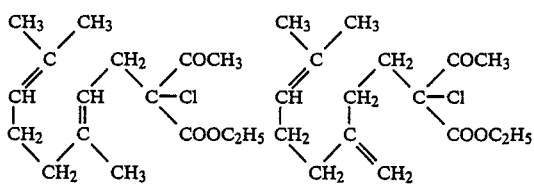

(Ia₂); 45%   (Ib₂); 55% b.p. $_{0.027}$ kPa (mixture) = 129° C.
chlorine content (mixture) = 11.8%.

The degree of conversion of the mixture of (IIa₂) and (IIb₂) is equal to 91%; the selectivity in respect of (Ia₂) and (Ib₂) is equal to 100%.

The mixture of the compounds (IIa₂) and (IIb₂) can be prepared in the following manner:

[RhCl.(cycloocta-1,5-diene)]₂ (100 mg; 0.41 milligram atom of rhodium), TppTSNa (0.78 g; 1.15 milligram atoms of $P^{3+}$) sodium carbonate (0.156 g; 1.5 millimols) and water (30 cc) are introduced into a stainless steel reactor purged with argon beforehand. Myrcene (8.8 g; 64.7 millimols) and ethyl acetylacetate (16.5 g; 127 millimols) are then introduced. The mixture is heated at 100° C. for 6 hours with stirring. After treatment of the reaction mixture, a mixture of (IIa₂) and (IIb₂) (12.66 g) is obtained.

EXAMPLE 3

Chlorination of a mixture of (IIa₃) and (IIb₃)

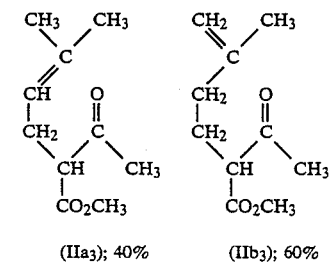

(IIa₃); 40%   (IIb₃); 60%

A mixture of the compounds (IIa₃) and (IIb₃) (18.87 g; 0.102 mol) is added to a mixture of cupric chloride (32.3 g; 0.24 mol) and lithium chloride (5.1 g; 0.12 mol) in N-methylpyrrolidone (100 cc). The reaction mixture is kept at 20° C. for 27 hours. After treatment of the reaction mixture as in Example 1, a mixture of (Ia₃) and (Ib₃) (21.57 g) is obtained, the purity of which is of the order of 88% and which has the following characteristics:

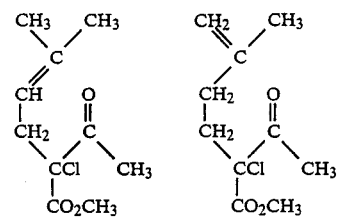

(Ia₃); 40%   (Ib₃); 60% b.p. $_{0.067}$ kPa (mixture) = 64° C.
chlorine content (mixture): 16.2%.

The degree of conversion of the mixture of (IIa$_3$) and (IIb$_3$) is equal to 88%; the selectivity in respect of (Ia$_3$) and (Ib$_3$) is equal to 100%.

The mixture of (IIa$_3$) and (IIb$_3$) can be prepared in the following manner:

[RhCl(cycloocta-1,5-diene)]$_2$ (20.8 mg; 0.085 milligram atom of rhodium), sodium carbonate (0.24 g; 2.2 millimols), TppTSNa (1.128 g; 1.7 milligram atoms of P$^{+3}$) and water (15 cc) are introduced into a stainless steel reactor purged with argon beforehand. Isoprene (10.2 g; 150 millimols) and methyl acetylacetate (21.6 g; 186 millimols) are then introduced. The mixture is heated at 100° C. for 1 hour with stirring. After treatment of the reaction mixture, a mixture of (IIa$_3$) and (IIb$_3$) (15.85 g) is obtained.

EXAMPLE 4

Chlorination of a mixture of (IIa$_1$) and (IIb$_1$)

A mixture of (IIa$_1$) and (IIb$_1$) (5.1 g; 0.020 mol) is added to a mixture of cupric chloride (5.38 g; 0.40 mol) and lithium chloride (0.87 g; 0.020 mol) in dimethylformamide (20 cc). The mixture is kept at 20° C. for 70 hours. After treatment of the reaction mixture as in Example 1, a mixture of (Ia$_1$) and (Ib$_1$) (5.26 g) is obtained, the purity of which is of the order of 60% and which has the following characteristics: (Ia$_1$); 45% (Ib$_1$); 55%

The degree of conversion of the mixture of (IIa$_1$) and (IIb$_1$) is equal to 62%; the selectivity in respect of (Ia$_1$) and (Ib$_1$) is equal to 100%.

EXAMPLE 5

The mixture of (Ia$_1$) and (Ib$_1$) obtained in Example 1 (2.56 g; 8.5 millimols) is added to lithium chloride (1 g; 0.0235 mol) in N-methylpyrrolidone (10 cc) and water (0.18 g; 0.010 mol). The mixture is kept under an inert argon atmosphere and is then heated at 100° C. for 45 minutes, with stirring; the decarboxylation is then complete. The heating is subsequently continued for 17 hours at the same temperature. After treatment of the reaction mixture by adding water (30 cc), extraction of the products with pentane (20 cc) and removal of the pentane under reduced pressure, a mixture (1.83 g) is obtained, which, according to analysis by gas chromatography (GC), contains pseudo-ionone (0.559 g), a mixture of products of formulae (VIIa$_1$) and (VIIb$_1$) (0.34 g), in which formulae R is the 4-methylpent-3-enyl radical, and heavy products not eluted in GC (0.6 g).

The degree of dehydrochlorination of (VII) is equal to 82% and the yield of (VI) is equal to 41.5%.

EXAMPLE 6

The mixture of (Ia$_1$) and (Ib$_1$) obtained in Example 1 (3.14 g; 0.011 mol) is added to lithium chloride (0.46 g; 0.0108 mol) in N-methylpyrrolidone (5 cc) and water (0.3 g; 0.0166 mol). The mixture is heated at 105° C. for 40 minutes. The reaction mixture then contains a mixture of (VIIal) and (VIIbl) (1.87 g; 0.0082 mol)

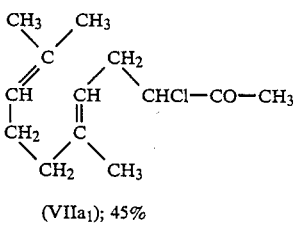

(VIIa$_1$); 45%

-continued

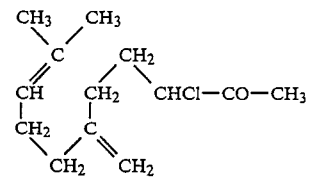

(VIIb$_1$); 55% b.p. $_{0.054 \, kPa}$ (mixture) = 93° C.

The degree of deacylation is of the order of 25%.

EXAMPLE 7

The mixture of (Ia$_1$) and (Ib$_1$) obtained in Example 1 (2.64 g; 9.2 millimols) is added to lithium chloride (0.5 g; 11.7 millimols) in N-methylpyrrolidone (5 cc) containing hydrochloric acid (0.49 g; 13.4 millimols). The mixture is heated at 105° C. for 2 hours 30 minutes. After treatment of the reaction mixture, a mixture of (VIIa$_1$) and (VIIb$_1$) (1.025g; 4.5 millimols) is obtained. Degradation products are formed and the degree of deacylation is of the order of 5%.

EXAMPLE 8

The mixture of (Ia$_1$) and (Ib$_1$) obtained in Example 1 (2.64 g; 9.2 millimols) is added to lithium chloride (0.5 g; 11.7 millimols) in N-methylpyrrolidone (5 cc) containing hydrochloric acid (0.13 g; 3.6 millimols). The mixture is heated at 130° C. for 2 hours with stirring. The decarboxylation is complete after 15 minutes. After treatment of the reaction mixture, pseudo-ionone (0.716 g) is obtained with a yield of 40.5%. The degree of deacylation is of the order of 5%. About 28% of heavy products not eluted in GC are formed.

The selectivity in respect of pseudo-ionone is equal to 57.4% for a degree of dehydrochlorination equal to 70.6%.

EXAMPLE 9

The mixture of (Ia$_1$) and (Ib$_1$) obtained in Example 1 (2.22 g; 9.5 millimols) is added to lithium chloride (5.0 g; 11.7 millimols) in N-mathylpyrrolidone (5 cc) containing hydrochloric acid (0.19 g; 5.7 millimols). The mixture is kept under an argon atmosphere and is then heated at 140° C. for 1 hour with stirring. The decarboxylation is complete after 15 minutes.

After treatment of the reaction mixture, pseudo-ionone (0.734 g) is obtained with a yield of 40%. The degree of deacylation is of the order of 5%. About 18% of heavy products not eluted in GC are formed.

The selectivity in respect of pseudo-ionone is equal to 60.6% for a degree of dehydrohalogenation of 66%.

EXAMPLE 10

2,4,6-Trimethylpyridine (1.27 g; 10.5 millimols) and the mixture of (Ia$_1$) and (Ib$_1$) obtained in Example 1 (2.58 g; 9 millimols) are added to lithium chloride (0.5 g; 11.7 millimols) in N-methylpyrrolidone (5 cc) containing hydrochloric acid (0.44 g; 12 millimols). The mixture is then heated at 130° C. for 4 hours with stirring. The decarboxylation is complete after 15 minutes. After treatment of the reaction mixture, pseudo-ionone (0.909 g) is obtained with a yield of 52.5%. The degree of deacylation is less than 1%. About 2.5% of heavy products not eluted in GC are formed.

The selectivity in respect of pseudo-ionone is equal to 90% for a degree of dehydrochlorination of 58.1%.

EXAMPLE 11

2,4,6-Trimethylpyridine (1.26 g; 10.5 millimols) and the mixture of (Ia$_1$) and (Ib$_1$) obtained in Example 1 (2.70 g; 9.4 millimols) are added to lithium chloride (0.5 g; 11.7 millimols) in N-methylpyrrolidone (10 cc) containing hydrochloric acid (0.46 g; 12.6 millimols). The mixture is heated at 130° C. for 8 hours with stirring. The decarboxylation is complete after 15 minutes. After treatment of the reaction mixture, pseudo-ionone (1.069 g) is obtained with a yield of 59.7%.

The degree of deacylation is less than 1%. About 12% of heavy products not eluted in GC are formed.

The selectivity in respect of pseudo-ionone is equal to 62.5% for a degree of dehydrochlorination of 95.50%.

EXAMPLE 12

The procedure of Example 11 is followed, but 20 cc of N-methylpyrrolidone are used. Pseudo-ionone (1.274 g) is obtained with a yield of 69.7%.

The degree of deacylation is less than 1%. About 9% of heavy products not eluted in GC are formed.

The selectivity in respect of pseudo-ionone is equal to 75.5% for a degree of dehydrochlorination of 92.4%.

EXAMPLE 13

The mixture of (Ia$_1$) and (Ib$_1$) obtained in Example 1 (2.70 g; 9.4 millimols) is added to lithium chloride (0.5 g; 11.7 millimols) in N-methylpyrrolidone (20 cc) containing hydrochloric acid (0.45 g; 12.3 millimols). The mixture is then heated at 150° C. for 2 hours 30 minutes with stirring. The decarboxylation is complete after 10 minutes. After treatment of the reaction mixture, pseudo-ionone (0.509 g) is obtained with a yield of 28.2%.

The degree of deacylation is less than 1%. About 10.5% of heavy products not eluted in GC are formed.

The selectivity in respect of pseudo-ionone is equal to 29.3% for a degree of dehydrochlorination of 96.2%.

EXAMPLE 14

The procedure of Example 13 is followed, but 2,4,6-trimethylpyridine (1.26 g; 10.5 millimols) and the mixture of (Ia$_1$) and (Ib$_1$) obtained in Example 1 (2.55 g; 8.9 millimols) are added. Pseudo-ionone (1.218 g) is obtained with a yield of 71.2%.

The degree of deacylation is less than 1%. About 11% of heavy products not eluted in GC are formed.

The selectivity in respect of pseudo-ionone is equal to 73.2% for a degree of dehydrochlorination of 97.2%.

EXAMPLE 15

The procedure of Example 13 is followed, but 2,4,6-trimethylpyridine (2.83 g; 23.3 millimols) and the mixture of (Ia$_1$) and (Ib$_1$) obtained in Example 1 (2.66 g; 9.3 millimols) are added. Pseudo-ionone (1.366 g) is obtained with a yield of 76.2%.

The degree of deacylation is less than 1%. About 12.5% of heavy products not eluted in GC are formed.

The selectivity in respect of pseudo-ionone is equal to 79% for a degree of dehydrochlorination of 96.5%.

EXAMPLE 16

The procedure of Example 13 is followed, but ethyldicyclohexylamine (4.25 g; 22.7 millimols) and the mixture of (Ia$_1$) and (Ib$_1$) obtained in Example 1 (2.66 g; 9.3 millimols) are added.

Pseudo-ionone (1.385 g) is obtained with a yield of 77.4%.

The degree of deacylation is less than 1%. About 1% of heavy products not eluted in GC are formed.

The selectivity in respect of pseudo-ionone is equal to 85.7% for a degree of dehydrochlorination of 90.4%.

EXAMPLE 17

2,4,6-Trimethylpyridine (1.29 g; 10.6 millimols) and the mixture of (VIIa$_1$) and (VIIb$_1$) obtained in Example 6 (1.94 g; 8.5 millimols) are added to lithium chloride (0.5 g; 11.7 millimols) in N-methylpyrrolidone (20 cc). The mixture is heated at 150° C. Pseudo-ionone (1.44 g) is obtained with a yield of 88%.

About 6.5% of heavy products not eluted in GC are formed.

The selectivity in respect of pseudo-ionone is equal to 94.6% for a degree of dehydrochlorination of 93%.

EXAMPLE 18

The procedure of Example 13 is followed, but ethyldicyclohexylamine (4.82 g; 23 millimols) and the mixture of (Ia$_2$) and (Ib$_2$) obtained in Example 2 (2.70 g; 9 millimols) are added.

Pseudo-ionone (1.377 g) is obtained with a yield of 79.9%.

The degree of deacylation is less than 1%. About 2% of heavy products not eluted in GC are formed.

The selectivity in respect of pseudo-ionone is equal to 90.2% for a degree of dehydrochlorination of 88.6%.

EXAMPLE 19

The mixture of (Ia$_1$) and (Ib$_1$) obtained in Example 1 (2.72 g; 9.5 millimols) is added to lithium chloride (0.5 g; 11.7 millimols) in tetramethylurea (20 cc) containing hydrochloric acid (0.5 g; 13.7 millimols). The mixture is then heated at 150° C. for 2 hours 30 minutes, with stirring. The decarboxylation is complete after 15 minutes. After treatment of the reaction mixture, pseudo-ionone (1.0 g) is obtained with a yield of 55.9%.

The degree of deacylation is less than 1%. About 5% of heavy products not eluted in GC are formed.

The selectivity in respect of pseudo-ionone is equal to 80% for a degree of dehydrochlorination of 68.4%.

EXAMPLE 20

Ethyldicyclohexylamine (64.52 g; 0.31 mol) and the mixture of the products (Ia$_3$) and (Ib$_3$) obtained in Example 3 (32.77 g; 0.15 mol) are added to lithium chloride (6.45 g; 0.15 mol) in N-methylpyrrolidone (250 cc) containing hydrochloric acid (5.77 g; 0.16 mol). The mixture is then heated at 150° C. for 3 hours 30 minutes, with stirring. The decarboxylation is complete after 10 minutes. After treatment of the reaction mixture, methylheptadienone of the formula (VIa$_2$)

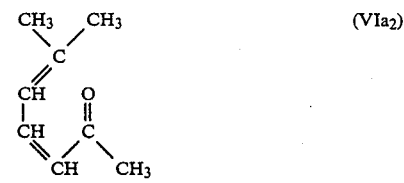

(14.237 g) is obtained with a yield of 75.5%.

The degree of deacylation is less than 1%. About 7% of heavy products not eluted in GC are formed.

The selectivity in respect of methylheptadienone of the formula (VIa₂) is equal to 79% for a degree of dehydrochlorination equal to 95.6%.

EXAMPLE 21

Ethyldicyclohexylamine (4.18 g; 20 millimols) and the mixture of the products (Ia₁) and (Ib₁) obtained in Example 1 (2.72 g; 9.5 millimols) are added to lithium chloride (0.5 g; 11.7 millimols) in dimethylformamide (20 cc) containing hydrochloric acid (0.42 g; 11.5 millimols). The mixture is then heated at 150° C. for 2 hours 30 minutes with stirring. The decarboxylation is complete after 15 minutes. After treatment of the reaction mixture, pseudo-ionone (1.079 g) is obtained with a yield of 59.3%.

The degree of deacylation is less than 1%. About 6.5% of heavy products not eluted in GC are formed.

The selectivity in respect of pseudo-ionone is equal to 80% for a degree of dehydrochlorination equal to 74.1%.

I claim:

1. A chlorinated β-ketoester of the formula:

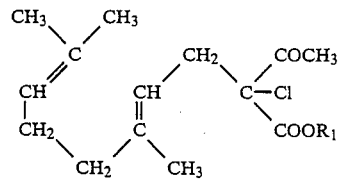

or

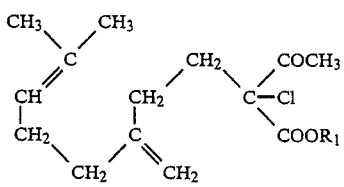

wherein R1 represents alkyl of 1 through 4 carbon atoms.

* * * * *